US00PP35172P2

(12) United States Plant Patent
Reynbery et al.

(10) Patent No.: US PP35,172 P2
(45) Date of Patent: May 16, 2023

(54) ***CANNABIS* PLANT NAMED 'PCT11204V'**

(50) Latin Name: *Cannabis sativa*
Varietal Denomination: PCT11204V

(71) Applicant: Phylos Bioscience, Inc., Portland, OR (US)

(72) Inventors: Jared Reynbery, Portland, OR (US); Alisha Holloway, Portland, OR (US); Erica Bakker, Portland, OR (US); John McFerson, Minneapolis, OR (US)

(73) Assignee: Phylos Bioscience, Inc., Portland, OR (US)

( * ) Notice: Subject to any disclaimer, the term of this patent is extended or adjusted under 35 U.S.C. 154(b) by 0 days.

(21) Appl. No.: 17/693,084

(22) Filed: Mar. 11, 2022

(51) Int. Cl.
*A01H 5/02* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258, 263.1
CPC ..... A01H 5/02; A01H 5/00; A01H 5/12
See application file for complete search history.

(56) References Cited

U.S. PATENT DOCUMENTS

| | | | |
|---|---|---|---|
| PP33,210 | P3 | 6/2021 | Kahn et al. |
| PP33,211 | P3 | 6/2021 | Kahn et al. |
| PP33,212 | P3 | 6/2021 | Kahn et al. |
| 11,297,789 | B2 | 4/2022 | Kahn et al. |
| 11,297,790 | B2 | 4/2022 | Kahn et al. |
| 11,297,791 | B2 | 4/2022 | Kahn et al. |
| 2020/0323162 | A1 | 10/2020 | Kahn et al. |
| 2020/0323163 | A1 | 10/2020 | Kahn et al. |
| 2020/0323164 | A1 | 10/2020 | Kahn et al. |
| 2020/0329599 | P1 | 10/2020 | Kahn et al. |
| 2020/0329600 | P1 | 10/2020 | Kahn et al. |
| 2020/0329601 | P1 | 10/2020 | Kahn et al. |

OTHER PUBLICATIONS

Welling, MT et al. (2019) "Complex Patterns of Cannabinoid Alkyl side-Chain Inheritance in Cannabis." Scientific Reports 9:11421.

Welling, MT et al (2020) "An extreme-phenotype genome-wide association study identifies candidate cannabinoid pathway genes in Cannabis" Scientific Reports 10:18643.

*Primary Examiner* — Kent L Bell
(74) *Attorney, Agent, or Firm* — Gregory C. Ellis

(57) ABSTRACT

A new and distinct variety of *Cannabis sativa* designated 'PCT11204V' as herein described and illustrated, characterized by elevated levels of THCV and other varin cannabinoids.

1 Drawing Sheet

Genus/species: *Cannabis sativa.*
Variety denomination: 'PCT11204V'.

BACKGROUND OF THE INVENTION

*Cannabis* plants contain over a hundred known cannabinoids, which bind to endogenous endocannabinoid receptors. Varinolic cannabinoids, known as varins, are a type of cannabinoid compound having three carbon atoms in their alkyl side chain instead of the five carbon atom alkyl side chains more commonly associated with cannabinoids. Two such varins are tetrahydrocannabivarin (THCV) and cannabidivarin (CBDV), which are homologues of tetrahydrocannabinol (THC) and cannabidiol (CBD), respectively. Each varin has a unique pharmacological profile and distinct molecular targets.

THCV and CBDV have potential benefits across a broad set of applications. *Cannabis* plants or extracts with high THCV levels, for example, can be used as an agent for anticonvulsant activity, obesity-associated glucose intolerance, appetite suppression, anxiety management for PTSD, diabetic neuropathy, and major neuropathic and pain related pathologies. Another THCV application is that of an appetite suppressing compound. CBDV has been shown to have anti-epileptic and anticonvulsant activity.

Research and development as well as the sale of varin products has been limited due to low commonly occurring levels of varins in *Cannabis* flower. The ability to produce *Cannabis* with high varin levels will create a platform for a new Cannabinoid category with differentiated, high margin products in both medical and recreational markets. The present invention solves these problems by providing a novel *Cannabis* plant having high varin levels, which is referred to by the variety name 'PCT11204V'.

BRIEF SUMMARY OF THE INVENTION

The new variety of *Cannabis sativa* was created by sourcing *Cannabis* plants that produce THCV. All breeding, cultivation, and chemotype analyses were conducted by a contract research organization under contract for the Applicant. Crosses were then conducted to elevate further THCV and other varins. The plants are crossed to produce new varieties that are selected to further elevate THCV levels. Progeny are chemically analyzed to select those having elevated THCV levels, and then either (1) backcrossed to the high-yielding THCV parent to ensure additional progeny can be selected for increased THCV production, or (2) selfed to fix genetic loci associated with THCV levels to ensure additional progeny can be selected for increased THCV production. Marker-assisted selection may be used further to identify candidate progeny expected to have elevated THCV levels for subsequent crosses to ensure selection of progeny having the highest THCV levels. All chemical analyses were conducted using High Performance Liquid Chromatography to detect the cannabinoids described herein. The present invention is a selection resulting from the cross of a high THCV pollen receiver plant ("20VLDY-1002-3") and a high THC pollen donor plant ("20TP1B-1008-1"). Parent cultivar 20VLDY-1002-3 is a late maturing (>12 weeks) cultivar with long internode lengths, flowers with low trichome density, a THCV content of 4-6%, and a THC content of 4-6%. Parent cultivar 20TP1B-1008-1 is similar to typical cultivated cultivars, with a maturity of 9 weeks from flower initiation, moderate internode lengths, a THC content of 21%, and a THCV content of 1%. Ninety seeds of variety "THC-Victory" were planted Aug 17, 2020. From this population, one plant designated "20VLDY-1002-3" of THC content 11.9% and THCV content 13.96% was selected and cloned for future crosses. 24 seeds of variety "Guicy Banger" were planted Jun. 19, 2020. From this population, one plant designated "20TP1B-1008-1" of THC content 20.66% and THCV content 1.16% was selected and cloned for future crosses. A clone of 20TP1B-1008-1 was crossed onto a clone of 20VLDY-1002-3 in the spring of 2021. 144 of the resulting F1 seeds were sown May 14, 2021. The present invention was discovered and selected as a single plant from this F1 seed and was subsequently propagated clonally at a contract research organization under contract for the Applicant. The selection was subsequently evaluated for five cycles at a contract research organization under contract for the Applicant. Individual plants were propagated in an indoor facility with supplemental lighting. Plants are transferred to a mixed-light greenhouse once established. Asexual reproduction of the new variety by stem cutting propagation since 2021 at the contract research organization under contract for the Applicant, and has demonstrated that the new variety reproduces true to type with all the characteristics, as herein described and are, firmly fixed and retained through successive generations of asexual propagation.

The new variety is named 'PCT11204V' and is characterized as having elevated varin levels.

BRIEF DESCRIPTION OF THE PHOTOGRAPH

FIG. 1 is a color image of the entire plant of a 89 day old flowering plant of the variety 'PCT11204V' taken at a contract research organization under contract for the Applicant.

DETAILED BOTANICAL DESCRIPTION

The following is a detailed description of the new *Cannabis* variety known as 'PCT11204V'.

All breeding, cultivation, and chemotype analyses were conducted by a contract research organization under contract for the Applicant.

*Cannabis* plants having elevated THCV levels were sourced and obtained, and crosses were conducted to further elevate THCV levels. The plants were crossed to produce new varieties that were selected to further elevate THCV levels. Plant variety 'PCT11204V' was selected and asexually reproduced.

Table 1 describes the general characteristics of 'PCT11204V' at 60 days after lighting was changed to a 12/12 light cycle. Color codes are derived from The Royal Horticultural Society (R.H.S.) Color Chart.

TABLE 1

| | |
|---|---|
| Plant life forms | An herbaceous plant (herb) |
| Plant growth habit | An upright, tap-rooted annual plant, forming fibrous roots when asexually propagated |
| Plant origin | A controlled cross between female parent 20VLDY-1002-3 (unpatented) and male parent 20TP1B-1008-1 (unpatented) |
| Plant propagation | Asexually propagated by replanting of apical and sub-apical semi-heraceous stem cuttings |
| Propagation Ease | Easy |
| Height | 1-1.3 m |
| Width | 0.7-0.9 m |
| Plant shape | Simple erect |
| Time to harvest | 10-12 weeks |
| Resistance to pests or diseases | Unknown |
| GMO? | No |

Table 2 describes the leaf/foliage of 'PCT11204V'.

TABLE 2

| | |
|---|---|
| Leaf Arrangement | Alternate |
| Leaflet Type | Palmately compound |
| Leaflet Structure | Serrated margins, lightly acicular to lanceolate leaflets, tapering to an acuminate apex |
| Leaflet Margins and Base | Margins are jaggedly serrate with each tooth apex angled toward leaflet apex; and base is attenuate. |
| Leaflet hairs | Present on both upper and lower surfaces |
| Leaf length with petiole at maturity | 14-22 cm |
| Petiole length and diameter at maturity | Length is 3.6-6.5 cm and diameter is 1-2 mm |
| Petiole color | 45C |
| Anthocyanin color and intensity in Petioles | Color is 47C and intensity in Petioles is medium in vegetative stage; strong in flowering stage |
| Stipule length and width at maturity | Length is 0.3-0.7 cm width is <1 mm |
| Stipule shape | Linear with slight curvaceous growth |
| Stipule color | 149C |
| No. of leaflets | 3-7 |
| Middle largest (longest) leaflet length | 11.5-15.2 cm |
| Middle largest (longest) leaflet width | 2.5-3.2 cm |
| Middle largest (longest) leaflet length/width ratio | 4.5-4.8 |
| No. teeth of middle leaflet | 20-26 |
| Leaflet (upper side-adaxial) color | 140A |
| Leaflet (lower side-abaxial) color | 135D |
| Leaflet glossiness | Slightly glossy on the upper surface |
| Vein/midrib shape | Obliquely continuous throughout leaflet |
| Vein/midrib color | 149D |
| Venation pattern | Pinnately veined leaflets |
| Aroma | Pleasantly pungent aromatic, strong, peculiar smell with a hint of cleaning solution scent |

Table 3 describes the stem of 'PCT11204V'.

TABLE 3

| | |
|---|---|
| Stem description | Hollow and ribbed |
| Stem diameter at base | 1.5 cm |
| Stem color | 142A |
| Stem length | 90-110 cm |

TABLE 3-continued

| | |
|---|---|
| Stem texture | Smooth with shallow grooves |
| Stem strength | Strong and upright |
| Depth of main stem ribs/grooves | Shallow |
| Internode length | 2.5-10 cm |

Table 4 describes the inflorescence of 'PCT11204V'.

TABLE 4

| | |
|---|---|
| Inflorescence type | Elongated compound cymes with the natural flowering season being Autumn |
| Proportion of female plants | 100% pistillate |
| Inflorescence position | Terminal and axillary |
| Inflorescence number per plant | 100-150 |
| Inflorescence length | 2-10 cm |
| Flower arrangement | Cymose |
| Numbers of flowers per plant | Hundreds to thousands flowers per plant, multitudinous, congested with high concentrations on bushier wide inflorescence |
| Flower shape | Urceolate |
| Flower (individual pistillate) length | 5-6 mm |
| Flower (compound cyme) diameter | 8.5-10.0 cm |
| Typical and observed flower depth | 2-4 mm |
| Corolla | No defined corolla |
| Corolla color | N/A |
| Bract shape | Urceolate |
| Bract color upper surface | 135C |
| Bract color lower surface | 135C |
| Bract number | 3-200 bracts per inflorescence |
| Bract length | 3-5 mm |
| Bract width | 2-3 mm |
| Bract apex | Caudate apex |
| Bract base descriptors | Rounded base |
| Bract texture | Smooth and covered with sticky trichomes |
| Calyx shape | No defined calyx |
| Calyx color | N/A |
| Stigma shape | Acute |
| Stigma length | 5-7 mm |
| Stigma width | <1 mm |
| Stigma color | 140B |
| Number of stigmas per flower | 2 |
| Trichome shape | Capitate-stalked glandular |
| Trichome color | NN155B |
| Terminal bud shape | Oblong |
| Terminal inflorescence length | 18-24 cm |
| Terminal inflorescence diameter | 7-10 cm |
| Terminal bud color | 140A, 140B, and 140C |
| Pedicel | Absent |
| Peduncle length | 1-8 mm |
| Peduncle diameter | 2-3 mm |
| Peduncle texture | Lightly ribbed |
| Peduncle color | 145A |
| Staminate shape | No staminate flowers produced naturally; however, male flower (staminate) can be induced with stress or ethylene-blocking compounds |
| Sepal color | NA |
| Pollen description | NA |
| Seed shape | Striped, smooth and globular |
| Seed size | 1.6 - 2.3 mm |

TABLE 4-continued

| | |
|---|---|
| Petal description | Apetalous |
| Pistil number per flower | one |
| Pistil length | 10-12 mm |
| Bracteole | Not present |

Table 5 describes other characteristics of 'PCT11204V'.

TABLE 5

| | |
|---|---|
| Time period of flowering/blooming | 10-12 weeks |
| Proportion of hermaphrodite plants | Lower (<5%) in clones |
| Hardiness of plant | Hardy to tolerate of warm and dry conditions without showing stress. Not tolerant to soil oversaturated with water for long periods |

Chemical analyses were conducted using High Performance Liquid Chromatography to detect the cannabinoids described herein. Table 6 describes a chemotype and terpene analysis of 'PCT11204V', which was chemotyped by taking a sample from the main cola at day 83 after initiation of the 12:12 light cycle, which initiates flowering. Trichomes were 65% cloudy and 1% amber, indicative of full maturity at sampling.

TABLE 6

Cannabinoid data for 'PCT11204V' (day 83 after flowering onset).

| Cannabinoid | % wt |
|---|---|
| Tetrahydrocannabivarinic acid (THCVA) | 15.6 |
| THCV | 0.28 |
| Total THCV | 140 |
| Cannabidivarinic acid (CBDVA) | 0.1 |
| CBDV | <LOD |
| Total CBDV | 0.09 |
| Total THCV + Total CBDV (= Total Varins) | 14.0 |
| Total THC + Total CBD (= Total Cannabinoids) | 11.9 |
| Total Varins/Total Cannabinoids | 1.18 |
| Tetrahydrocannabinolic acid (THCA) | 13.3 |
| Delta-9-tetrahydrocannabinol (D9-THC) | 0.2 |
| Total THC | 11.9 |
| Cannabidiolic acid (CBDA) | <LOD |
| CBD | <LOD |
| Total CBD | <LOD |
| THC:CBD ratio | Undefined value due to null value in denominator |
| beta-myrcene | 0.9-2.8% |
| beta-caryophyllene | 0.3-0.5% |
| ocimene | 0.3-0.8% |
| bisabolol | 0.08-0.14% |
| alpha-humulene | 0.08-0.15% |

"<LOD" refers to an undetectable analyte that is below the limit of detection.

What is claimed is:

1. A new and distinct variety of *Cannabis sativa* plant designated 'PCT11204V' as herein described and illustrated.

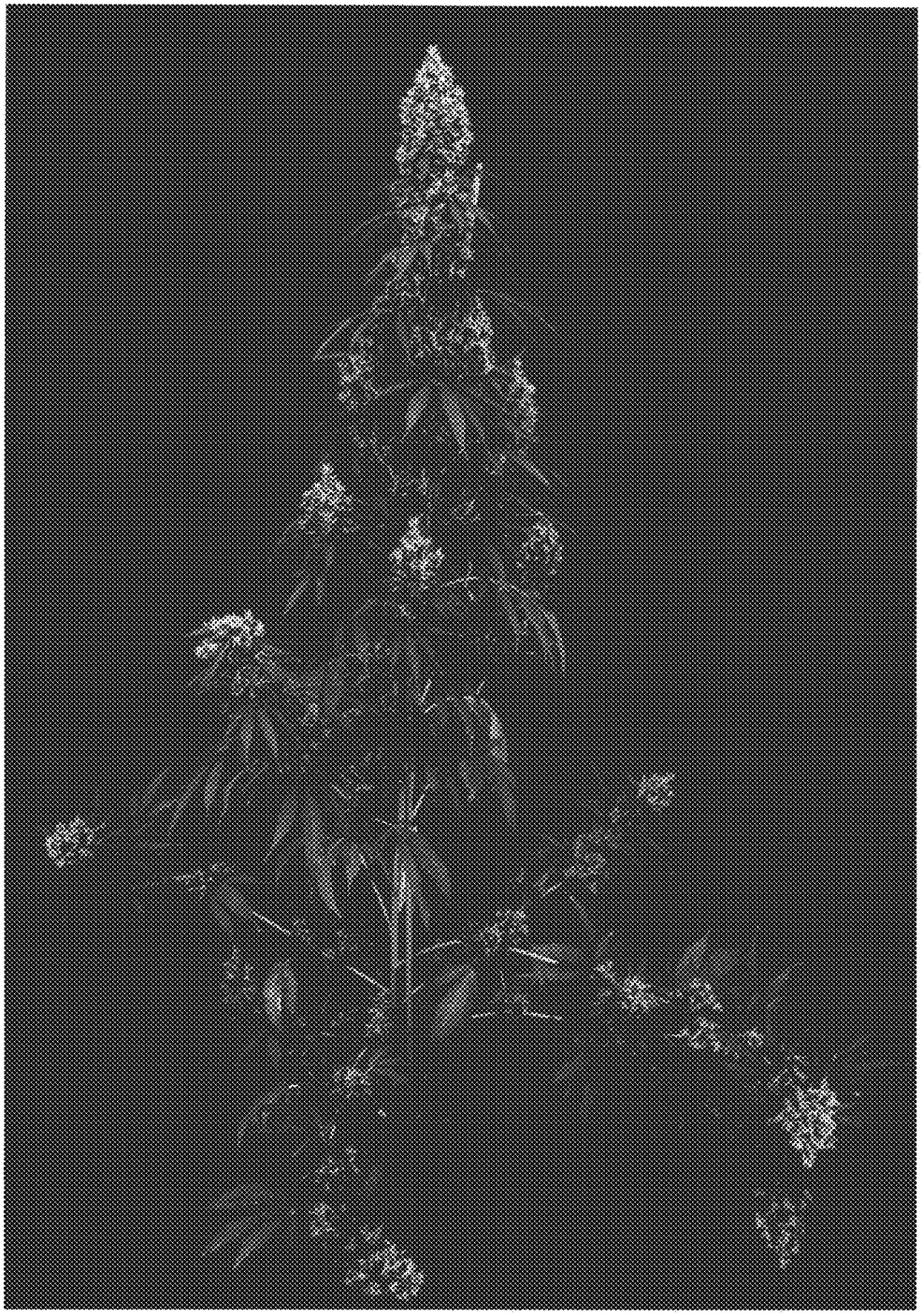

* * * * *